United States Patent [19]

Neri

[11] 4,194,289
[45] Mar. 25, 1980

[54] AIR AND WATER SUPPLY SYSTEM FOR DENTAL HANDPIECES

[76] Inventor: Vincenzo Neri, Corso Galileo Ferraris 104, Turin, Italy

[21] Appl. No.: 944,223

[22] Filed: Sep. 20, 1978

[30] Foreign Application Priority Data

Sep. 22, 1977 [IT] Italy ................. 69093 A/77

[51] Int. Cl.² ............................................. A61C 19/02
[52] U.S. Cl. .................................................... 433/101
[58] Field of Search ................... 32/22; 137/637.1, 87

[56] References Cited

U.S. PATENT DOCUMENTS

| | | | |
|---|---|---|---|
| 3,755,899 | 9/1973 | Betush | 32/22 |
| 3,875,958 | 4/1975 | Miller | 137/87 |
| 3,924,660 | 12/1975 | Woodhams | 137/637.1 |
| 4,069,587 | 1/1978 | Peralta | 32/22 |

OTHER PUBLICATIONS

Progressive Machine Products Co., 2209 Federal Ave., Los Angeles, Calif. 90064, "Proma 360", Systems and Vertifour, 3 pp., Dec. 77.

*Primary Examiner*—Robert Peshock
*Attorney, Agent, or Firm*—C. Hercus Just

[57] ABSTRACT

A pneumatically operated system for controlling the supply of water and/or water and air simultaneously to an air turbine-type dental handpiece, either to only drive the handpiece or drive it and simultaneously provide a spray. Two foot-actuated valves respectively controlling the supply of air to a handpiece are connected to a source of air under pressure and are respectively connected to a compound servo-control valve including a spool operable in a housing between various inlet and outlet ports for air which, when one foot-actuated valve is opened, will cause the spool to move from an initially inoperative position to afford delivery of drive air only to the handpiece and when the second foot-actuated valve is opened, additional air is by-passed at the same spool setting from one part of the housing to another part containing a normally closed water valve connected to water under pressure and opened by said additional air which actuates a small piston that engages said water valve to open it. The handpiece is supported in a holder by which the spool is maintained in said inoperative position. Springs restore the spool and small piston to their initial inoperative positions.

6 Claims, 6 Drawing Figures

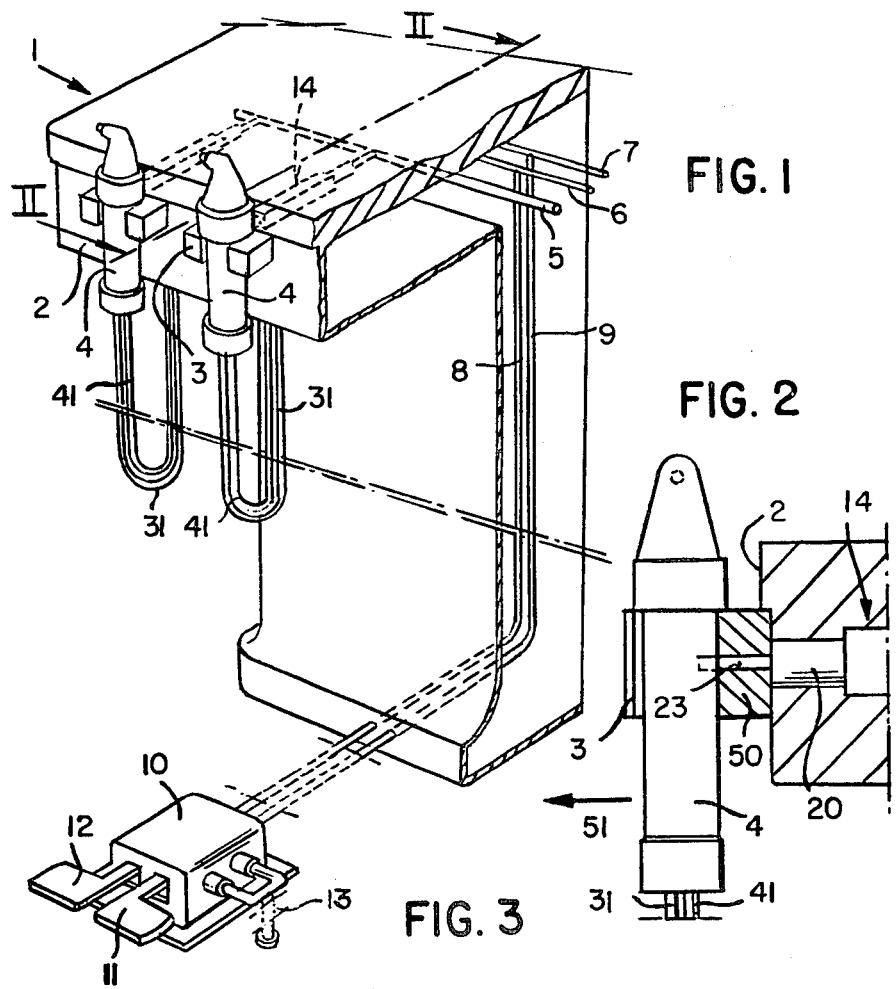
FIG. 1
FIG. 2
FIG. 3
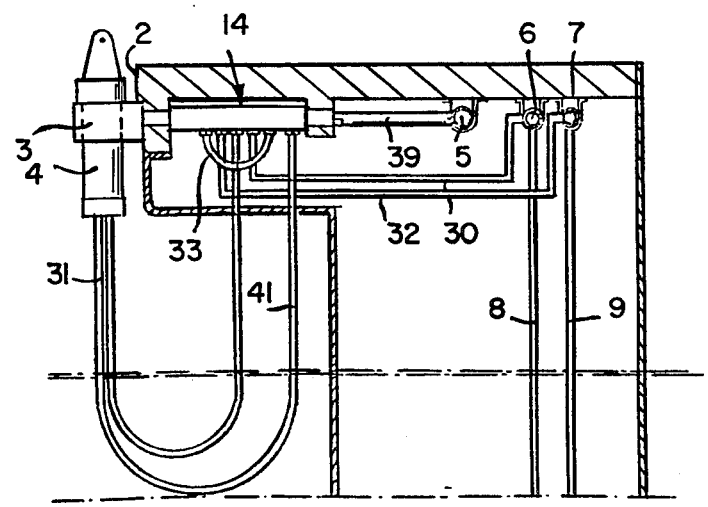

AIR AND WATER SUPPLY SYSTEM FOR DENTAL HANDPIECES

BACKGROUND OF THE INVENTION

Systems for the control of the supply of air under pressure and water to dental handpieces are already known, particularly to several drills operated by turbines, for which it is possible to supply air under pressure to the handpiece by depressing a suitable pedal, or simultaneously water and air under pressure required to activate the turbine and to provide a water spray, by depressing another suitable pedal.

Since by depressing the above-mentioned pedals, air under pressure, or water and air under pressure, are available simultaneously to all handpieces of the type mounted on a suitable support near the chair for the patient, steps are taken to permit the effective flow only to the handpiece which, at any given time, is removed from the support for use. In this manner, one avoids the flow of air under pressure and eventually water and air under pressure to the handpieces that are not being used and which remain in their respective supports and no air activates the handpieces not in use.

The above special steps involve the use of valves incorporated or otherwise mounted on the bracket which holds the support onto which the handpieces are hung. The valves remain closed when the handpieces are left in said supports.

The mechanical systems are made in the form of supports shaped like a lever or balance-spring which move under the weight of the handpieces against the action of a spring-loaded mechanism for closing the valve for the air under pressure and for water.

Also known are techniques which include ball bearings which are pressed against a seat to impede the flow of air under pressure and water to the respective tubings which lead to the handpiece. The removal of a handpiece from the relative support permits the movement of the ball bearings and the restoration of the flow of air and water under pressure to the handpiece itself.

Other more modern systems embody the use of fluidic valves having sensors which emerge in the supports and are obstructed by the handpieces when the latter are placed in said supports.

The above-mentioned known systems present numerous problems. The problem common to all is the presence of a valve operated by a pedal for the control of the flow of water to the handpieces. In case of failure, due for example to a damaged seal, there is the risk of flooding the office in which the equipment is installed, and it is not possible to correct the problem without obtaining the assistance of technical personnel.

In addition, the valve systems, the opening and closings of which depend on whether or not the handpiece is hung on the support, present additional inconveniences which add to the problem mentioned above. Therefore, for example, mechanical systems are not too dependable and are easily subject to failures which require the attention of specialized personnel to be repaired.

The fluidic valves, two of which are required for each handpiece, are very expensive and if there is a failure, even though they do not occur too frequently, they require the attention of experts to be repaired or replaced.

SUMMARY OF THE INVENTION

The present invention has the object to provide a system to control the supply of air under pressure and of water to dental handpieces, which is free of the above-mentioned problems and which, even though its cost is moderate, it is distinguished from other systems by a very high long-lasting reliability. In addition, it will allow repairs or maintenance to be performed by personnel in a dental office without the intervention of technicians.

According to this invention, these objects are obtained through the provision of a system for the control of the supply of air under pressure and of water to at least one dental handpiece, particularly to a drill operated by a turbine. The system is of the type which comprises a first foot-operated control valve placed in the circuit between the handpiece and the source of air under pressure, which connects the latter source with the handpiece when a first pedal is depressed and, for every handpiece, a first intercepting valve, placed downstream from said first control valve and a second intercepting valve inserted in the circuit which connects the handpiece to a source of water supply, which can be operated only when the respective handpiece is removed from the corresponding support, and including finally a second pedal, the activation of which causes the opening of said second intercepting valve, characterized by the fact that it includes, for each handpiece, a servo-pneumatic mechanism which will open said second intercepting valve if air pressure is applied thereto. Said servo-pneumatic mechanism is capable of being connected with the source of pressurized air by depressing a second foot-operated control valve which normally connects to atmosphere instead of access to said second auxiliary intercepting valve normally closed but which opens under the action of air under pressure when the air is allowed to flow to the handpiece by the operation of said first control valve to connect said first intercepting valve with the source of air under pressure through said first control valve.

Other characteristics and advantages of the invention will be quite clear from the following description, which is only exemplary and a non-limiting example of a preferred operation thereof which is illustrated in the attached drawings.

BRIEF DESCRIPTION OF THE DRAWINGS

FIG. 1 is a perspective view of the system which, in accordance with the invention, is applied to several handpieces.

FIG. 2 is a schematic section taken along line II—II of FIG. 1.

FIG. 3 is a section which shows, in enlarged scale, details of the structure illustrated in FIGS. 1 and 2.

DETAILED DESCRIPTION

Figure 4:
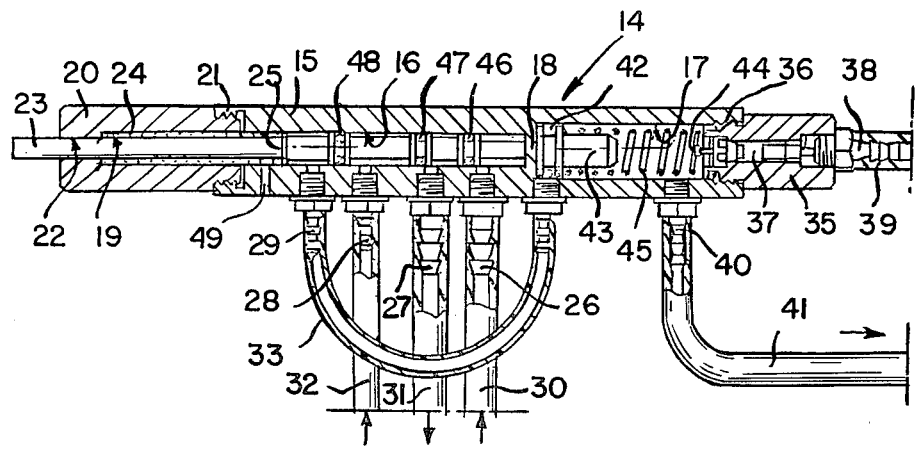
FIG. 4 is a longitudinal section which shows one of the components of the system in accordance with the invention in the rest position.

In FIG. 1, the frame 1 of the apparatus has a tabletop appearance and a front panel 2 to which are affixed supports 3 for the handpieces 4. The latter are handpieces of various types, including turbines activated by compressed air with provisions for the projection of water spray toward the working area of the bur in such handpieces.

Inside the frame 1, at the height of the tabletop, are mounted conduit tubes 5, 6 & 7, which extend throughout the entire length of the framework itself. Tube 5 is connected to a potable water spray in the handpieces (not illustrated). Tubes 6 and 7 are connected respectively to other tubes 8 and 9, which are flexible at least where they exit from the base of the frame 1 and normally are connected at the outer end to flow control valves of conventional type (not illustrated) contained in housing 10, and when the foot pedals 11 and 12 thereon are activated, air will be delivered from tube 13 which is connected with a source of air under pressure, for example from the tank of a compressor.

Figure 5:
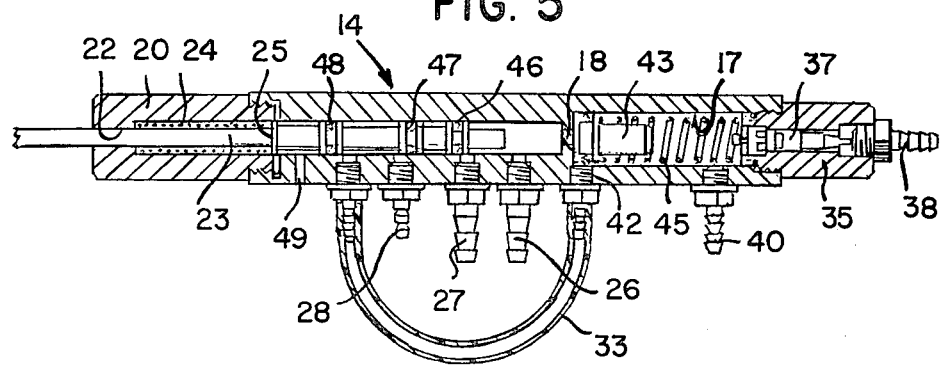
FIGS. 5 and 6 are longitudinal sections of the component illustrated in FIG. 3, which depicts it in two successive phases of operation.
Figure 6:
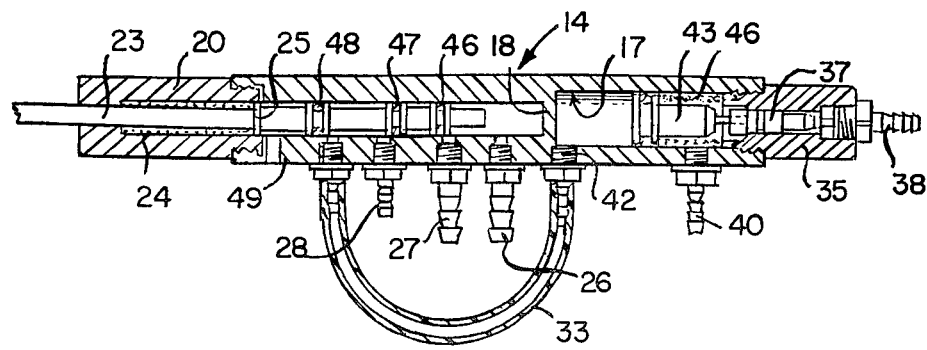

To each support 3 is attached a group of servo-controlled valves 14, illustrated in greater detail in FIGS. 4-6.

Every group of servo-controlled valves 14 consists of a central body 15, preferably of a square-shaped cross-section. Inside such body there are two axial cavities, see FIGS. 4-6, respectively 16 and 17, of a circular-shaped cross-section, separated by a transverse wall 18. The axial cylindrical cavity 16 extends to one end of the body 15 and connects at that point with the internal opening of the same diameter 19 of a threaded bushing 20. The latter is connected to the body 15 through threads 21 and has a guide bearing opening 22 at its end 22 to guide the end of a cylindrical rod 23 located in the interconnecting cavities 16 and 19. The end of this rod, opposite to the end which is guided in opening 22 is disposed in the normal rest or in inoperative position in the unit 14 as shown in FIG. 3, against the transverse wall 18 through the action of a helical spring 24 placed between the opening 22 of the bushing 20 and a peripheral flange 25 on the rod 23.

One of the lateral sides of body 15 has four ports in which tubular fittings, respectively 26, 27, 28 and 29, are connected for communication with the inside of cavity 16 which contains rod 23. Tube 30 is connected to fitting 26. The former is connected to tube 6 and through the latter to tube 8 with the first control valve (not illustrated) controlled by pedal 11. On fitting 27 the end of flexible tube 31 is connected and the other end of this tube is attached to handpiece 4 to deliver driving air to the turbine of the handpiece. On fitting 28, tube 32 is connected which connects said fitting with water delivery tube 7, which, in turn, is connected through tube 9 to the control valve (not illustrated) in housing 10 that is actuated by pedal 12 to supply pressurized air to central body 15.

Fitting 29 is, in turn, connected through a short tube 33 to fitting 34 which connects, through a hole in the wall of body 15 located near the transverse wall 18, with the inside of cavity 17. This cavity is closed, in relation to the end opposite to wall 18, by a bushing 35 drilled axially and connected to body 15 by threads 36.

A servo-control valve unit 14 comprises a small valve 37 which is inserted in the axial opening of bushing 35 and normally is closed against the flow in the direction of cavity 17. The bushing 35 has a tubular fitting 38 at the end opposite cavity 17 which communicates with the axial hole of bushing 35. Tube 39 is on bushing 38 and connects with the water supply tube 5. Body 15 also has an additional tubular fitting 40 which connects with cavity 17 through a hole in the wall of body 15 in the area near the end of bushing 35 which is opposite the transverse wall 18 that divides cavities 16 and 17. A flexible tube 41 is attached to fitting 40 and the other end of the tube is connected to the water tube of the handpiece, which leads to the spray opening thereof.

Reciprocable within cavity 17, there is a small piston 43 made water-tight by an O-ring 42. The small piston has an end which protrudes in the direction of the small valve 37 located in bushing 35 which also has a stem 44 protruding inside cavity 17 past the end of bushing 35 facing said cavity. The small piston 43 is held close to the transverse wall 18 by the action of a relatively weak helical spring 45 between the piston and bushing 35. Naturally, the dimensions of the small piston 43 and the position of the round hole which connects fittings 34 with the inside of cavity 17 are such that, upon arrival of fluid under pressure through small tube 33, such fluid fills the space between O-ring 42 and the transverse wall 18, creating a force which moves the small piston 43 against the action of spring 45 and into contact with stem 44 of valve 37.

On rod 23, located in the interconnecting cavities 16 and 19, which are on the other side of transverse wall 18 from servo-control valve 14, there are 3 O-ring seals, respectively 46, 47 and 48. Said seals are stationary upon rod 23 due to being mounted between pairs of spaced circular flanges which define together with rod 23 ring-shaped seals for the above-mentioned seals. The axial distance between seals 46, 47 and 48, the distance of seal 46 from the end of rod 23 facing the transverse wall 18, and the reciprocal distances and the dimensions of the holes connected with fittings 26, 27, 28 and 29, are such that when rod 23 is in the rest or inoperative position, illustrated in FIG. 3, seals 46 and 47 can be moved in the direction of bushing 20 in respect to the holes connected with fittings 26 and 27 to establish communication between tubes 30 and 31 by passage of fluid between seal 46 and wall 18 and also effect the flow between fittings 28 and 29. The distances between the axes of the holes connecting with fittings 27, 28 and 29 and the dimensions of these holes are also designed in such a way that the seals 46 and 47 can be located between the holes connecting with fittings 27 and 28 in such a way to control the flow between such fittings.

Simultaneously, seal 48 is positioned to the side of the hole connected with fitting 29 nearer bushing 20 but moved in the direction of the transverse wall 18 in respect to hole 49 which connects cavity 16 with atmosphere.

The length of rod 23 is such that it protrudes somewhat past the external end of bushing 20. The protrusion corresponds to the thickness of part 50 of support 3 (see FIG. 3) onto which normally handpiece 4 is hung when it is not being used.

The system functions as follows: When pedal 11 is depressed, the opening of the respective valves contained in housing 10 allows air under pressure to pass through tubes 8, 6 and 30, in the part of cavity 16 between O-ring 46 and transverse wall 18, thus creating a force which moves stem 23 outward against the action of spring 24. It must be noted, however, that such movement can take place only when handpiece 4 is removed from support 3 which is connected with assembly 14. If this did not occur, the presence of the handpiece itself prevents, see FIG. 3, the movement of rod 23 against the action of spring 24. The support is designed in such a way that it will not permit a movement of handpiece 4 in relation to the support itself in the direction of the arrow 51, shown in FIG. 2, without first removing the handpiece in an upward direction.

If only pedal 12 is depressed, the respective valve therefor, located in housing 10 is activated and the air under pressure is allowed to flow in tubes 9, 7 and 32, see FIG. 3. However, there will be no movement of stem 23 if pedal 11 is not also depressed. Air under pressure will remain in fact captive in the space of cavity 16 between O-rings 47 and 48, and this independently from the fact of whether or not handpiece 4 is removed from support 3 or remains hung on it.

First, by depressing pedal 11, movement of one of the handpieces 4 from its support will cause movement of rod 23 against the action of spring 24 until it reaches the operative position illustrated in FIG. 5. In such position, seals 46 and 47, which act as the first intercepting valve 15, will assume such a position that the fittings 26 and 27 are interconnected and air under pressure will pass from tube 30 into tube 31 and from the latter to the handpiece, which, in turn, activates the turbine thereof. At the same time, seals 47 and 48, which act as a said second part of intercepting valve 15, will be in such a position to open the connection between fittings 28 and 29, isolating them both from the part of cavity 16 connected with the outside through hole 49, and from the hole connected with fitting 27 through which air under pressure flows to the handpiece.

Next, by depressing pedal 12, the control valve associated therewith in housing 10 is opened, the flow of air under pressure is opened, through tubes 9, 7 and 32 to the part of cavity 16 between seals 47 and 48. This causes the flow of air under pressure through tube 33 into a space between the transverse wall 18 and the O-ring seal 42 of the small piston 43, which then moves in cavity 17, and acts as a pneumatic servo-command of valve 37. Said small piston moves against the tension of the weak return spring 45, until it hits against stem 44 of valve 37 which, in opening, allows the water to flow, beginning from tubing 5 connected to the water distribution network, through tube 39 and fitting 38 into cavity 17 and from here, through fitting 40 and tube 41 to the handpiece.

By releasing the pressure on pedals 11 and 12, rod 23 returns toward the initial position indicated in FIG. 4. In such position, fitting 29 and with it small tube 33 and the space between the transverse wall 18 and the O-ring seal 42 of the small piston 43, which is in cavity 17, are connected to atmosphere through hole 49. This aids the return of the small piston 43 to the initial starting position illustrated in FIGS. 4 and 5, and thereby, forms a vacuum in cavity 17, after the return of stem 44 of the water intercepting valve 37 to closed position. This is advantageous inasmuch as it creates aspiration of water from the respective tubes in the handpiece. In addition, the presence of hole 49 facilitates the prompt return of rod 23 to the rest position.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A system operable to control the supply of air under pressure and water to a dental handpiece of the air turbine-type held when not in use upon a support, said system comprising in combination:

(a) a first foot-actuated control valve connectable in a circuit between a handpiece and a source of air under pressure,
   (b) a first intercepting valve downstream in said circuit with said first control valve and movable to open position to deliver air to drive said handpiece when said first foot-actuated valve is moved to open position to cause air to move said first intercepting valve to open position,
   (c) a second intercepting valve in a circuit between a handpiece and a source of water,
   (d) means connected to said first intercepting valve and adapted to be engaged by a handpiece when held in rest position within a support to prevent moving said second intercepting valve to open position but rendering said valve movable to open position upon removing said handpiece from said support, and
   (e) a second foot-actuated control valve connectable to a source of air under pressure and in said circuit of said second intercepting valve, whereby when said second control valve is opened air is delivered to said second intercepting valve to open the same for delivery of water to said handpiece,
   (f) said movement of said second foot-actuated control valve being possible only when said first intercepting valve has been moved to open position to effect operation of said handpiece.

2. The system according to claim 1 in which said second intercepting valve comprises a servo-pneumatic system including in combination:

(a) a body having a cylindrical cavity,
   (b) a valve in one end of said cavity connectable to said source of water and having one end of a movable valve member extending into said cavity and spring pressed closed against a valve seat normally to prevent inlet of water into said cavity,
   (c) a first port and fitting in said cavity adjacent said valve and connectable to a flexible tube for connection to a handpiece to deliver water thereto,
   (d) a small piston movable axially within said cavity between the opposite end of said cavity and said one end of said valve member,
   (e) a second port and fitting in said cavity adjacent said one end thereof,
   (f) a conducting tube connected between said second port and fitting and said first intercepting valve and adapted to receive air under pressure therefrom when in open position to move said piston from adjacent said opposite end of said cavity into contact with said movable valve member to move the same to open position and thereby admit water into said cavity for discharge through said first port to a handpiece to effect a spray therefrom.

3. The system according to claim 1 in which said first intercepting valve comprises a body having an axial cavity extending between a fixed wall and a bushing threaded into said body at the opposite end of said cavity, said bushing having an axial bearing hole therethrough coaxial with said cavity and slidably receiving one end of a rod slidably movable within said cavity and having three axially spaced O-rings thereon within said cavity, said body having four axially spaced ports therethrough extending into said cavity and fittings secured therein for connection of conducting tubes thereto, said fittings having conducting tubes connected thereto considered in sequence from said fixed wall respectively to said first foot-actuated valve; a handpiece for air to drive the same; said second foot-actuated valve and said second intercepting valve when in initial inoperative position, having said O-rings located therein in seats on said rod in locations respectively between said first and second ports; said second and third ports; and said third and fourth ports, the latter being nearest said bushing, a spring engaging said rod and normally biasing it toward said fixed wall, and said first foot-actuated valve when opened causing air to be delivered to said first intercepting valve to move said rod against the action of said spring and dispose the first two O-rings respectively between said second and third ports to effect communication between said first and second ports to deliver driving air to said handpiece and dispose the third O-ring between said fourth port and bushing, thereby to effect communication between said third and fourth ports to cause air under pressure to be delivered to said second intercepting valve and actuate the same to cause delivery of water to said handpiece.

4. The system according to claim 3 in which the end of said rod which is disposed in said bushing is adjacent a holder for a handpiece and said rod normally is held in an inner inoperative position by engagement of a handpiece when in said holder with the outer end of said rod to prevent outward movement thereof to an operative position until the handpiece is removed from the holder therefor.

5. The system according to claim 3 in which the innermost movement of said rod into said body is determined by the inner end of said rod engaging said fixed wall in said body, and said system also including a compression spring surrounding the end portion of said rod nearest said bushing, one end of said spring abutting said bushing and said rod having a peripheral flange spaced from the nearest O-ring thereon and abutted by the opposite end of said spring, the strength of said spring being adequate to normally bias said rod into abutment with said end wall in said body.

6. The system according to claim 3 in which said body is elongated and said cavity also is elongated and parallel to the axis of said body, and said second intercepting valve comprises a servo-pneumatic system also contained within said body and including a cylindrical cavity coaxial with said aforementioned cavity and separated therefrom by a fixed wall within said body.

* * * * *